US009259260B2

(12) United States Patent
Greep et al.

(10) Patent No.: US 9,259,260 B2
(45) Date of Patent: Feb. 16, 2016

(54) FLUID EVACUATION DEVICE

(71) Applicant: Megadyne Medical Products, Inc., Draper, UT (US)

(72) Inventors: Darcy W. Greep, Herriman, UT (US); Chad S. Frampton, American Fork, UT (US)

(73) Assignee: Megadyne Medical Products, Inc., Draper, UT (US)

( * ) Notice: Subject to any disclaimer, the term of this patent is extended or adjusted under 35 U.S.C. 154(b) by 140 days.

(21) Appl. No.: 13/831,560

(22) Filed: Mar. 14, 2013

(65) Prior Publication Data

US 2014/0276469 A1 Sep. 18, 2014

(51) Int. Cl.
| | |
|---|---|
| *A61B 18/00* | (2006.01) |
| *A61M 1/00* | (2006.01) |
| *A61C 1/14* | (2006.01) |
| *A61B 18/14* | (2006.01) |
| *A61B 17/32* | (2006.01) |

(52) U.S. Cl.
CPC ............ *A61B 18/00* (2013.01); *A61B 18/1485* (2013.01); *A61C 1/141* (2013.01); *A61M 1/008* (2013.01); *A61B 17/320068* (2013.01); *A61B 2018/00595* (2013.01); *A61B 2018/00601* (2013.01); *A61B 2218/001* (2013.01)

(58) Field of Classification Search
CPC .......... A61C 1/141; A61C 1/147; A61C 1/10; A61C 1/12; A61B 2017/0042; A61B 2017/00424; A61B 2017/00455; A61B 2018/00601; A61B 2018/00916; B25F 1/02; B25F 1/04; B23B 45/00; F16P 3/18; B25G 1/102

USPC ..................................................... 606/41–42
See application file for complete search history.

(56) References Cited

U.S. PATENT DOCUMENTS

| | | | |
|---|---|---|---|
| 2,311,424 A | 2/1943 | Weller, Jr. | |
| 2,329,439 A | 9/1943 | Hanssen | |
| 2,426,214 A | 8/1947 | Hewes | |
| 2,530,962 A | 11/1950 | Hare | |
| 2,542,019 A | 2/1951 | Fischer | |
| 4,562,838 A * | 1/1986 | Walker ............................ | 606/42 |

(Continued)

FOREIGN PATENT DOCUMENTS

| | | |
|---|---|---|
| CA | 2107230 | 10/1992 |
| CA | 2111617 | 7/1994 |

(Continued)

OTHER PUBLICATIONS

U.S. Appl. No. 12/429,867, Feb. 3, 2012, Office Action.

(Continued)

*Primary Examiner* — Andrew Gilbert
(74) *Attorney, Agent, or Firm* — Workman Nydegger

(57) ABSTRACT

A fluid evacuation device is attachable to a hand-held instrument to provide the hand-held instrument with fluid evacuation capabilities. The fluid evacuation device includes a nozzle, a hose mount, and an evacuation hose. The nozzle has a receptacle that receives a portion of a hand-held instrument therein. The distal end of the nozzle has an opening therein through which fluid may be drawn into the nozzle. The fluid can pass through a flow region in the nozzle. The hose mount extends from the nozzle and connects the hose to the nozzle. The hose mount includes a passageway through which the fluid can pass from the flow region into the evacuation hose.

21 Claims, 8 Drawing Sheets

(56) References Cited

U.S. PATENT DOCUMENTS

| | | | |
|---|---|---|---|
| 4,683,884 A | 8/1987 | Hatfield | |
| 4,921,492 A | 5/1990 | Schultz et al. | |
| 5,066,294 A | 11/1991 | Cosmescu | |
| 5,085,657 A * | 2/1992 | Ben-Simhon | A61M 1/0084 604/35 |
| 5,088,997 A | 2/1992 | Delahuerga et al. | |
| 5,108,389 A | 4/1992 | Cosmescu | |
| 5,114,422 A | 5/1992 | Cosmescu | |
| 5,154,709 A * | 10/1992 | Johnson | 606/45 |
| 5,160,334 A | 11/1992 | Billings et al. | |
| 5,181,916 A | 1/1993 | Reynolds | |
| 5,192,267 A | 3/1993 | Shapira | |
| 5,195,959 A | 3/1993 | Smith | |
| 5,196,007 A | 3/1993 | Ellman et al. | |
| 5,197,963 A * | 3/1993 | Parins | A61B 18/1482 606/41 |
| 5,199,944 A | 4/1993 | Cosmescu | |
| 5,217,457 A | 6/1993 | Delahuerga et al. | |
| 5,224,944 A * | 7/1993 | Elliott | 606/41 |
| 5,244,462 A | 9/1993 | Delahuerga | |
| 5,302,354 A | 4/1994 | Watvedt et al. | |
| 5,304,763 A | 4/1994 | Ellman et al. | |
| 5,312,397 A | 5/1994 | Cosmescu | |
| 5,318,516 A | 6/1994 | Cosmescu | |
| 5,318,565 A | 6/1994 | Kuriloff | |
| 5,358,552 A | 10/1994 | Seibert et al. | |
| 5,423,779 A | 6/1995 | Yeh | |
| 5,427,570 A * | 6/1995 | Chen | F24C 15/2078 285/184 |
| 5,431,650 A | 7/1995 | Cosmescu | |
| 5,451,223 A | 9/1995 | Ben-Simhon | |
| 5,458,586 A | 10/1995 | Adiletta | |
| 5,460,602 A | 10/1995 | Shapira | |
| 5,507,535 A * | 4/1996 | McKamey | A61M 16/08 128/912 |
| 5,520,651 A | 5/1996 | Sutcu et al. | |
| D372,086 S | 7/1996 | Grasso et al. | |
| D373,190 S * | 8/1996 | Monson | D24/112 |
| 5,575,789 A | 11/1996 | Bell et al. | |
| 5,609,573 A | 3/1997 | Sandock | |
| 5,613,966 A | 3/1997 | Makower et al. | |
| 5,626,568 A | 5/1997 | Yeh et al. | |
| D384,148 S * | 9/1997 | Monson | D24/112 |
| 5,662,647 A | 9/1997 | Crow | |
| 5,674,219 A * | 10/1997 | Monson et al. | 606/45 |
| 5,693,044 A | 12/1997 | Cosmescu | |
| 5,769,702 A * | 6/1998 | Hanson | A61B 18/00 128/204.18 |
| 5,797,901 A | 8/1998 | Cosmescu | |
| 5,830,214 A | 11/1998 | Flom | |
| 5,836,909 A | 11/1998 | Cosmescu | |
| 5,836,944 A | 11/1998 | Cosmescu | |
| 5,868,722 A | 2/1999 | Yeh et al. | |
| 5,874,052 A | 2/1999 | Holland | |
| 5,928,137 A * | 7/1999 | Green | A61B 1/00052 600/104 |
| 6,001,077 A | 12/1999 | Ellman et al. | |
| 6,045,596 A | 4/2000 | Holland, Jr. et al. | |
| 6,053,886 A | 4/2000 | Holland, Jr. et al. | |
| D426,883 S * | 6/2000 | Berman et al. | D24/112 |
| 6,099,525 A | 8/2000 | Cosmescu | |
| 6,110,259 A | 8/2000 | Schultz et al. | |
| 6,117,134 A | 9/2000 | Cunningham | |
| 6,142,995 A | 11/2000 | Cosmescu | |
| 6,146,353 A | 11/2000 | Platt | |
| 6,149,648 A | 11/2000 | Cosmescu | |
| 6,231,571 B1 | 5/2001 | Ellman | |
| 6,293,945 B1 | 9/2001 | Parins | |
| 6,302,881 B1 | 10/2001 | Farin | |
| 6,306,135 B1 | 10/2001 | Ellman et al. | |
| 6,355,034 B2 | 3/2002 | Cosmescu | |
| 6,368,309 B1 | 4/2002 | Yeh | |
| 6,379,350 B1 | 4/2002 | Sharkey | |
| 6,391,027 B1 | 5/2002 | Farin | |
| 6,458,125 B1 | 10/2002 | Cosmescu | |
| 6,524,307 B1 * | 2/2003 | Palmerton et al. | 606/41 |
| 6,530,924 B1 | 3/2003 | Ellman | |
| 6,544,210 B1 | 4/2003 | Trudel et al. | |
| 6,576,033 B1 | 6/2003 | Booth | |
| 6,585,791 B1 | 7/2003 | Garito et al. | |
| 6,589,316 B1 | 7/2003 | Schultz et al. | |
| 6,602,249 B1 * | 8/2003 | Stoddard et al. | 606/45 |
| 6,616,658 B2 * | 9/2003 | Ineson | 606/42 |
| 6,635,034 B1 | 10/2003 | Cosmescu | |
| 6,663,610 B1 | 12/2003 | Thompson et al. | |
| 6,685,665 B2 | 2/2004 | Booth et al. | |
| 6,702,812 B2 | 3/2004 | Cosmescu | |
| 6,716,211 B2 | 4/2004 | Mulier | |
| 6,746,504 B2 | 6/2004 | Booth | |
| 6,749,608 B2 | 6/2004 | Garito et al. | |
| D493,530 S * | 7/2004 | Reschke | D24/144 |
| 6,802,842 B2 | 10/2004 | Ellman | |
| 6,881,236 B2 | 4/2005 | Schultz et al. | |
| 6,923,804 B2 * | 8/2005 | Eggers | A61B 18/1206 606/34 |
| 6,942,650 B1 | 9/2005 | Schultz et al. | |
| 7,004,939 B2 | 2/2006 | MacKay | |
| 7,033,353 B2 | 4/2006 | Stoddard et al. | |
| 7,083,601 B1 | 8/2006 | Cosmescu | |
| 7,112,199 B2 | 9/2006 | Cosmescu | |
| 7,198,626 B2 | 4/2007 | Lee | |
| 7,207,977 B2 | 4/2007 | Thompson et al. | |
| 7,241,294 B2 | 7/2007 | Reschke | |
| 7,258,712 B2 | 8/2007 | Schultz et al. | |
| 7,261,711 B2 | 8/2007 | Mulier | |
| D555,803 S | 11/2007 | Garito et al. | |
| 7,294,116 B1 | 11/2007 | Ellman et al. | |
| 7,329,253 B2 | 2/2008 | Brounstein | |
| 7,387,625 B2 | 6/2008 | Hovda | |
| 7,393,351 B2 | 7/2008 | Woloszko | |
| 7,419,488 B2 | 9/2008 | Ciarrocca | |
| 7,435,247 B2 | 10/2008 | Woloszko | |
| 7,491,200 B2 | 2/2009 | Underwood | |
| 7,494,473 B2 | 2/2009 | Eggers | |
| 7,597,731 B2 | 10/2009 | Palmerton et al. | |
| 7,717,890 B2 | 5/2010 | Drogue et al. | |
| 7,717,912 B2 | 5/2010 | Woloszko | |
| D616,986 S | 6/2010 | Biegen et al. | |
| 7,761,188 B2 | 7/2010 | Palmerton et al. | |
| 7,789,946 B2 | 9/2010 | Schultz et al. | |
| 7,824,398 B2 | 11/2010 | Woloszko | |
| 7,828,797 B2 | 11/2010 | Eggers | |
| 7,892,337 B2 | 2/2011 | Palmerton et al. | |
| 7,935,109 B2 | 5/2011 | Cosmescu | |
| 7,959,698 B2 | 6/2011 | Schultz et al. | |
| 7,988,689 B2 | 8/2011 | Woloszko | |
| 8,002,732 B2 | 8/2011 | Visconti | |
| 8,057,470 B2 * | 11/2011 | Lee et al. | 606/41 |
| 8,095,241 B2 | 1/2012 | Palmerton et al. | |
| 8,137,345 B2 | 3/2012 | McNall | |
| 8,147,577 B2 | 4/2012 | Palmerton et al. | |
| 8,187,272 B2 | 5/2012 | Sensenbrenner | |
| 8,211,103 B2 * | 7/2012 | Greep | 606/42 |
| 8,235,982 B2 | 8/2012 | Ward | |
| 8,241,278 B2 | 8/2012 | Sartor | |
| 8,317,786 B2 | 11/2012 | Dahla | |
| 8,323,279 B2 | 12/2012 | Dahla | |
| 8,414,576 B2 * | 4/2013 | Cosmescu | 606/41 |
| 8,460,289 B2 | 6/2013 | Sartor | |
| 8,518,018 B2 | 8/2013 | Minskoff | |
| D709,196 S * | 7/2014 | Greep et al. | D24/144 |
| 2001/0018586 A1 | 8/2001 | Cosmescu | |
| 2001/0051804 A1 | 12/2001 | Mulier | |
| 2002/0013582 A1 | 1/2002 | Mulier | |
| 2002/0019631 A1 * | 2/2002 | Kidder et al. | 606/42 |
| 2002/0049438 A1 | 4/2002 | Sharkey | |
| 2002/0058938 A1 | 5/2002 | Cosmescu | |
| 2002/0103485 A1 | 8/2002 | Melnyk | |
| 2003/0030328 A1 * | 2/2003 | Tamai | H01R 31/06 307/82 |
| 2003/0135208 A1 | 7/2003 | Luigi | |
| 2003/0181904 A1 | 9/2003 | Levine | |
| 2003/0181934 A1 * | 9/2003 | Johnston | A61B 17/162 606/167 |

(56) References Cited

U.S. PATENT DOCUMENTS

| | | | |
|---|---|---|---|
| 2004/0049183 A1 | 3/2004 | Ellman | |
| 2004/0162553 A1 | 8/2004 | Peng | |
| 2005/0107782 A1 | 5/2005 | Reschke | |
| 2005/0113825 A1 | 5/2005 | Cosmescu | |
| 2005/0124986 A1 | 6/2005 | Brounstein | |
| 2006/0264928 A1* | 11/2006 | Kornerup et al. | 606/45 |
| 2006/0276783 A1 | 12/2006 | Cosmescu | |
| 2007/0129722 A1* | 6/2007 | Cosmescu | 606/42 |
| 2007/0249990 A1 | 10/2007 | Cosmescu | |
| 2007/0255272 A1 | 11/2007 | Ariola | |
| 2007/0265615 A1 | 11/2007 | Ben-Simhon | |
| 2008/0103431 A1 | 5/2008 | Brounstein | |
| 2009/0018539 A1* | 1/2009 | Cosmescu | 606/41 |
| 2009/0062791 A1 | 3/2009 | Lee | |
| 2009/0069802 A1 | 3/2009 | Garito | |
| 2009/0125023 A1* | 5/2009 | Stephen et al. | 606/42 |
| 2010/0076411 A1* | 3/2010 | Wu | 604/540 |
| 2010/0094200 A1 | 4/2010 | Dean et al. | |
| 2010/0094283 A1 | 4/2010 | Cosmescu | |
| 2010/0174283 A1 | 7/2010 | McNall | |
| 2011/0077645 A1 | 3/2011 | Lin | |
| 2011/0190768 A1 | 8/2011 | Shvetsov et al. | |
| 2012/0101497 A1 | 4/2012 | Jayaraj | |
| 2012/0143186 A1 | 6/2012 | McNall | |
| 2012/0180664 A1 | 7/2012 | Lundquist | |
| 2012/0197250 A1 | 8/2012 | Ward | |
| 2012/0203223 A1 | 8/2012 | Terry | |
| 2012/0283718 A1 | 11/2012 | Cosmescu | |
| 2012/0283728 A1 | 11/2012 | Cosmescu | |
| 2012/0286179 A1 | 11/2012 | Palmerton et al. | |
| 2013/0006236 A1* | 1/2013 | Greep et al. | 606/34 |
| 2013/0110108 A1 | 5/2013 | Davison | |
| 2013/0204246 A1* | 8/2013 | Greep et al. | 606/41 |
| 2014/0046321 A1 | 2/2014 | Zinnanti | |

FOREIGN PATENT DOCUMENTS

| | | |
|---|---|---|
| CA | 2241516 | 7/1997 |
| CA | 2200535 | 9/1997 |
| CA | 2311424 | 7/1999 |
| CA | 2542019 | 7/1999 |
| CA | 2329439 | 10/1999 |
| CA | 2351649 | 5/2000 |
| CA | 2707676 | 5/2000 |
| CA | 2352880 | 8/2000 |
| CA | 2426214 | 5/2002 |
| CA | 2462825 | 4/2003 |
| CA | 2530962 | 1/2005 |
| CA | 2123960 | 7/2005 |
| CA | 2557280 | 10/2005 |
| CA | 2541694 | 10/2006 |
| CA | 2613950 | 11/2007 |
| CA | 2604402 | 3/2008 |
| CA | 2639108 | 2/2009 |
| CA | 2009151831 | 5/2009 |
| EP | 0447121 | 9/1991 |
| EP | 0538641 | 4/1993 |
| EP | 1016383 | 7/2000 |
| EP | 1188415 | 3/2002 |
| EP | 1388324 | 2/2004 |
| EP | 1532928 | 5/2005 |
| EP | 1584342 | 10/2005 |
| EP | 1707146 | 10/2006 |
| EP | 1795139 | 6/2007 |
| EP | 1902682 | 3/2008 |
| EP | 1938767 | 7/2008 |
| EP | 2438876 | 4/2012 |
| ES | 2159778 | 10/1998 |
| ES | 2238776 | 9/2005 |
| GB | 1457411 | 12/1976 |
| IL | 136254 | 3/1998 |
| IL | 139085 | 11/2001 |
| IL | 125102 | 7/2003 |
| IL | 159929 | 6/2004 |
| WO | 9108797 | 12/1990 |
| WO | 9108797 | 6/1991 |
| WO | 9219168 | 11/1992 |
| WO | 9623448 | 1/1996 |
| WO | 9619151 | 6/1996 |
| WO | 9723167 | 7/1997 |
| WO | 9931954 | 7/1999 |
| WO | 9953833 | 10/1999 |
| WO | 0028908 | 5/2000 |
| WO | 0032296 | 6/2000 |
| WO | 0238033 | 5/2002 |
| WO | 02060314 | 8/2002 |
| WO | 03030714 | 4/2003 |
| WO | 2005007214 | 1/2005 |
| WO | 2005094710 | 1/2005 |
| WO | 2005028078 | 3/2005 |
| WO | 2005046498 | 5/2005 |
| WO | 2007005159 | 1/2007 |
| WO | 2007123565 | 11/2007 |
| WO | 2008109014 | 9/2008 |
| WO | 2012/154699 | 5/2012 |
| WO | 2012155922 | 11/2012 |

OTHER PUBLICATIONS

U.S. Appl. No. 12/429,867, Mar. 6, 2012, Notice of Allowance.
International Search Report and Written Opinion PCT/US2014/28094 dated Sep. 18, 2014.

* cited by examiner

FLUID EVACUATION DEVICE

BACKGROUND

1. Technical Field

This invention relates to fluid evacuation devices. More particularly, the invention relates to fluid evacuation devices that may be selectively attached to other instruments.

2. The Relevant Technology

As is known to those skilled in the art, modern surgical techniques typically employ radio frequency (RF) power to cut tissue and coagulate bleeding encountered in performing surgical procedures. For a historical perspective and details of such techniques, reference is made to U.S. Pat. No. 4,936,842, issued to D'Amelio et al., and entitled "Electroprobe Apparatus," the disclosure of which is incorporated by this reference.

As is known to those skilled in the medical arts, electrosurgery is widely used and offers many advantages including the use of a single surgical instrument for both cutting and coagulation. A monopolar electrosurgical generator system has an active electrode, such as in the form of an electro surgical instrument having a hand piece and a conductive electrode or tip, which is applied by the surgeon to the patient at the surgical site to perform surgery and a return electrode to connect the patient back to the generator.

The electrode or tip of the electrosurgical instrument is small at the point of contact with the patient to produce an RF current with a high current density in order to produce a surgical effect of cutting or coagulating tissue. The return electrode carries the same RF current provided to the electrode or tip of the electrosurgical instrument, thus providing a path back to the electrosurgical generator.

To make the electrical connection for the RF current between the electrosurgical generator and the electrosurgical instrument, a cable having an electrically conductive core extends from the electrosurgical generator to the electrosurgical instrument. The cable may also include a cord with additional conductors. The cord provides a connection for transmitting control signals from the electrosurgical instrument to the electrosurgical generator. The control signals may be used to cause the generator to deliver RF currents to the electrosurgical instrument for different cutting modes such as cut, coagulate, and cut-coagulate blend.

When an electrosurgical instrument is used for cutting or coagulation, smoke is commonly produced. A surgeon or assistant often uses a separate smoke evacuation device to remove the smoke from the surgical field. Smoke evacuation devices commonly include a suction wand connected to a vacuum device via tubing. The surgeon or assistant holds the suction wand close to the surgical site and the smoke is drawn into the suction wand and through the tubing. However, using a smoke evacuation device separate from the electrosurgical instrument is not ideal. Using a separate smoke evacuation device requires additional hands and instruments near the surgical site, which can obscure the surgeon's view of the surgical site and reduce the room available around the surgical site for the surgeon to move.

As a result, combination electrosurgical instrument and smoke evacuation devices have been developed. These combination devices often include a hand piece that can receive an electrode tip for performing electrosurgical procedures. The hand piece is connected to a generator via a power cable to convey RF current to the electrode tip. Additionally, a smoke evacuation hose is connected between the hand piece and a vacuum device to draw smoke away from the surgical site. In some cases, the power cable runs through a portion of the smoke evacuation hose.

The power cables and smoke evacuation hoses have certain flexibility and weight characteristics that limit the ability of the physician during a surgical procedure. For example, the weight/moment-arm effect and drag of the power cable and/or the smoke evacuation hose as well as the connection location(s) of the power cable and/or smoke evacuation hose to the electrosurgical instrument limit the physician's ability to continually hold and use the electrosurgical instrument. The electrode tip is received within one end of the hand piece (commonly referred to as a pencil) and the power cable and/or smoke evacuation hose typically enter into the opposite end of the hand piece. As the physician manipulates the electrosurgical instrument during a surgical procedure, the weight of the power cable and/or smoke evacuation hose continually pulls on the end of the electrosurgical instrument to which it is attached. More specifically, as the physician adjusts the orientation of the electrosurgical instrument so as to bring the electrode into contact with the patient's tissue, the weight of the power cable and/or smoke evacuation hose resists the physician's movement. The constant resistance or drag created by the power cable and/or smoke evacuation hose can cause the physician to become fatigued during a surgical procedure that requires extensive and continual use of the electrosurgical instrument.

Additionally, many electrosurgical procedures are performed on very sensitive parts of the body, such as on or around the eyes. When performing such procedures, the physician must control the movements of the electrode with great precision and accuracy. The resistance or drag created by the power cable and/or smoke evacuation hose can make it more difficult for the physician to be as precise and accurate. For instance, when moving the electrosurgical instrument to make a delicate incision, the physician must accurately compensate for the resistance from the power cable and/or smoke evacuation hose. If the physician overcompensates, an incision that is too deep or too long can result. Alternatively, if the physician undercompensates, multiple passes may be required to achieve the desired incision. Furthermore, the fatigue caused by the resistance from the power cable and/or smoke evacuation hose can adversely affect the physician's ability to accurately compensate for the resistance from the power cable and/or smoke evacuation hose.

While combination electrosurgical instrument and smoke evacuation devices may reduce or eliminate the need to use a separate smoke evacuation device, as noted above, combination electrosurgical instrument and smoke evacuation combination devices have various drawbacks. As noted above, the hoses and cables of such instruments create resistance to the movement of the instruments. Furthermore, there are numerous electrosurgical instruments already being used that do not provide smoke evacuation capabilities. Thus, transitioning to a combination electrosurgical instrument and smoke evacuation device would require the purchase of an entirely new instrument that includes both the electrosurgical and smoke evacuation capabilities. Thus, while the combination devices may address some of the foregoing drawbacks, such as requiring the use of separate instruments to perform multiple functions, current combination devices do not address the resistance issues discussed above or the ability to retrofit existing hand-held instruments with fluid evacuation capabilities.

Thus, there remains room for improvement with regards to electrosurgical and smoke evacuation devices. Nevertheless, the subject matter claimed herein is not limited to embodiments that solve any disadvantages or that operate only in environments such as those described above. Rather, this background is only provided to illustrate one exemplary technology area where some embodiments described herein may be practiced.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION

The present invention generally relates to attachments for hand-held instruments or hand pieces. More specifically, embodiments of the present invention relate to fluid evacuation devices that can be selectively attached to a hand-held instrument or hand piece to effectively provide the hand-held instrument or hand piece with fluid evacuation capabilities in addition to the original capabilities of the hand-held instrument or hand piece. The fluid evacuation device can also facilitate the performance of various procedures while reducing the amount of fatigue experienced by users performing the procedures.

In most electrosurgical instruments that are manufactured or retrofitted with an evacuation hose, the evacuation hose is connected to and/or extends away from a proximal end of the electrosurgical instrument. When the evacuation hose is connected to or extends from the proximal end of the electrosurgical instrument, the weight/moment-arm effect of the evacuation hose resists movement of the electrosurgical instrument. As discussed herein, such resistance can lead to fatigue in the user's hand. In contrast, the fluid evacuation device of the present invention connects to the distal end of an electrosurgical instrument. Additionally, an evacuation hose of the fluid evacuation device is able to extend from the electrosurgical instrument at one or more locations away from the proximal end of the electrosurgical instrument. As a result, the fluid evacuation device provides fluid evacuation capabilities without creating resistance that can fatigue the user.

Figure 1:
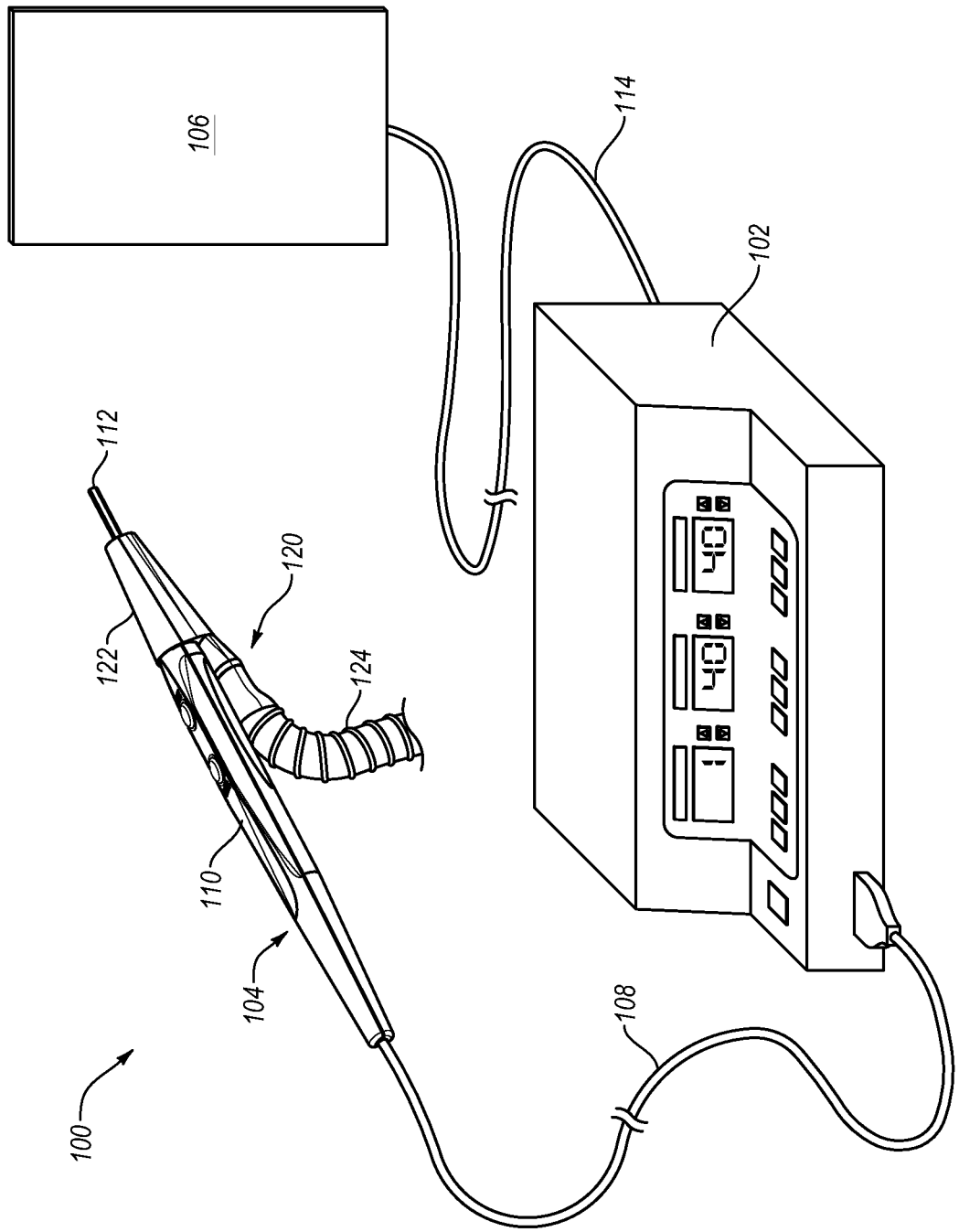
FIG. 1 illustrates an electrosurgical system, including an electrosurgical instrument retrofitted with a fluid evacuation device, according to one exemplary embodiment of the present invention.

Referring to FIG. 1, an exemplary environment is illustrated that provides one operating environment for use of the present invention. In FIG. 1, an electrosurgical system 100 is illustrated, which includes a signal generator 102, an electrosurgical instrument 104, and a return electrode 106. Generator 102, in one embodiment, is an RF wave generator that produces RF electrical energy and communicates the RF electrical energy to electrosurgical instrument 104 via cable 108.

Electrosurgical instrument 104 includes a hand piece or pencil 110 and an electrode tip 112. Electrosurgical instrument 104 communicates the RF electrical energy to a patient to cut tissue and/or cauterize blood vessels of the patient's body. Specifically, an electrical discharge is delivered from tip 112 to the patient in order to cause the heating of cellular matter of the patient that is in extremely close contact to tip 112. The heating takes place at an appropriately high temperature to allow electrosurgical instrument 104 to be used to perform electrosurgery. Return electrode 106 and cable 114 provide a return electrical path to wave generator 102 for any excess charge that dissipates into surrounding tissue of the patient's body.

Also illustrated in FIG. 1 is a fluid evacuation device 120 that can be selectively connected to electrosurgical instrument 104 to effectively provide electrosurgical instrument 104 with fluid evacuation capabilities. As used herein, the term "fluid" may refer to liquids, gases, vapors, smoke, or combinations thereof. Fluid evacuation device 120 may be used to evacuate or remove fluid from a surgical site. For instance, fluid evacuation device 120 may be used to remove smoke, water, blood, and the like from a surgical site. In some embodiments, fluid evacuation device 120 may be used to deliver fluids to a surgical site.

Fluid evacuation device 120 includes a nozzle 122 that is selectively connectable to the distal end of electrosurgical instrument 104. In the illustrated embodiment, a distal end of hand piece 110 extends into a proximal end of nozzle 122 and electrode tip 112 extends out of a distal end of nozzle 122. Extending proximally from the proximal end of nozzle 122 is an evacuation hose 124. An opposing end of evacuation hose 124 may be connected to a vacuum device (not shown) so as to draw fluid into nozzle 122, through evacuation hose 124, and away from a surgical site.

Figure 2:
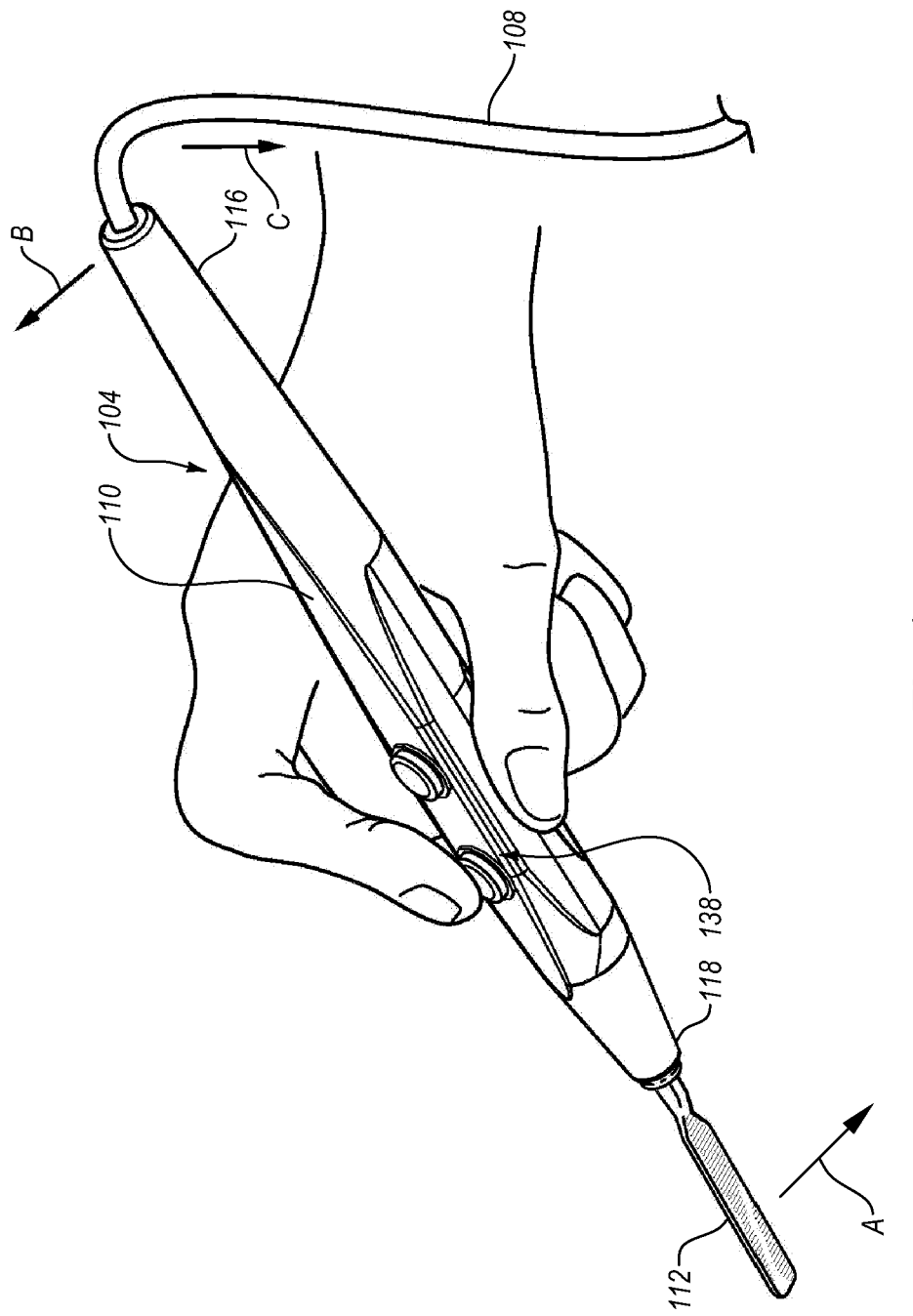
FIG. 2 illustrates one manner of holding an electrosurgical instrument.

Attention is now directed to FIG. 2, which illustrates one of the most common manners by which physicians hold electrosurgical instrument 104 during an electrosurgical procedure. As can be seen, hand piece 110 is laid through the crook of the hand and is held in place by the middle finger and thumb. The index finger is placed on top of hand piece 110 to further hold hand piece 110 in place as well as to activate input devices 138.

As noted elsewhere herein, the flexibility, weight/moment-arm and drag characteristics of cable 108 and the connection location of cable 108 to hand piece 110 limit the ability of the physician during a surgical procedure. While holding electrosurgical instrument 104 as shown in FIG. 2, a physician will perform electrosurgery by activating input devices 138 and moving electrode tip 112 into contact with the patient's tissue. To make contact between electrode tip 112 and the patient's tissue, the physician will move his or her wrist or fingers to adjust the position and/or orientation of electrosurgical instrument 104.

For instance, the physician may move his or her wrist so that electrode tip 112 moves in the direction of arrow A toward the patient's tissue. Notably, as the physician moves electrode tip 112 in the direction of arrow A, proximal end 116 moves in the direction of arrow B. The weight of cable 108 constantly pulls proximal end 116 in the direction of arrow C. Thus, the weight of cable 108 resists the movement of proximal end 116 in the direction of arrow B.

The resistance created by the weight of cable 108 is accentuated by the location at which cable 108 is connected to hand piece 110. As is understood, a torque is created by applying a force at a distance from an axis or pivot point. The magnitude of the torque is a result of the magnitude of the applied force and the distance between the axis/pivot point and the location where the force is applied. In the case of electrosurgical instrument 104, the weight of cable 108 is the force that contributes to the generation of the resistive torque. Additionally, the location at which cable 108 attaches to hand piece 110 and how hand piece 110 is held creates the lever arm through which the weight of cable 108 works to create the torque. More specifically, cable 108 enters hand piece 110 at or near proximal end 116. When electrosurgical instrument 104 is held as shown in FIG. 2, proximal end 116 is positioned above and away from the crook of the physician's hand, which acts as the pivot point. The weight of cable 108 pulls down on proximal end 116, thereby creating a torque or moment-arm. Because the magnitude of the torque is dependent on the distance between the pivot point and the force, the further apart the connection point between cable 108 and hand piece 110 is away from the crook of the hand, the greater the torque will be. Understandably, the larger the torque is, the greater amount of resistance the physician will experience when manipulating electrosurgical instrument 104.

To overcome the resistance created by the weight of cable 108, the physician must exert additional energy to move electrosurgical instrument 104 into the desired orientation. Continuously working against the resistance created by cable 108 can cause the physician's hand, and/or wrist, and/or arm to become fatigued during an electrosurgical procedure. This fatigue can also lead to a loss of accuracy and precision in the performance of the procedure.

Figure 3:
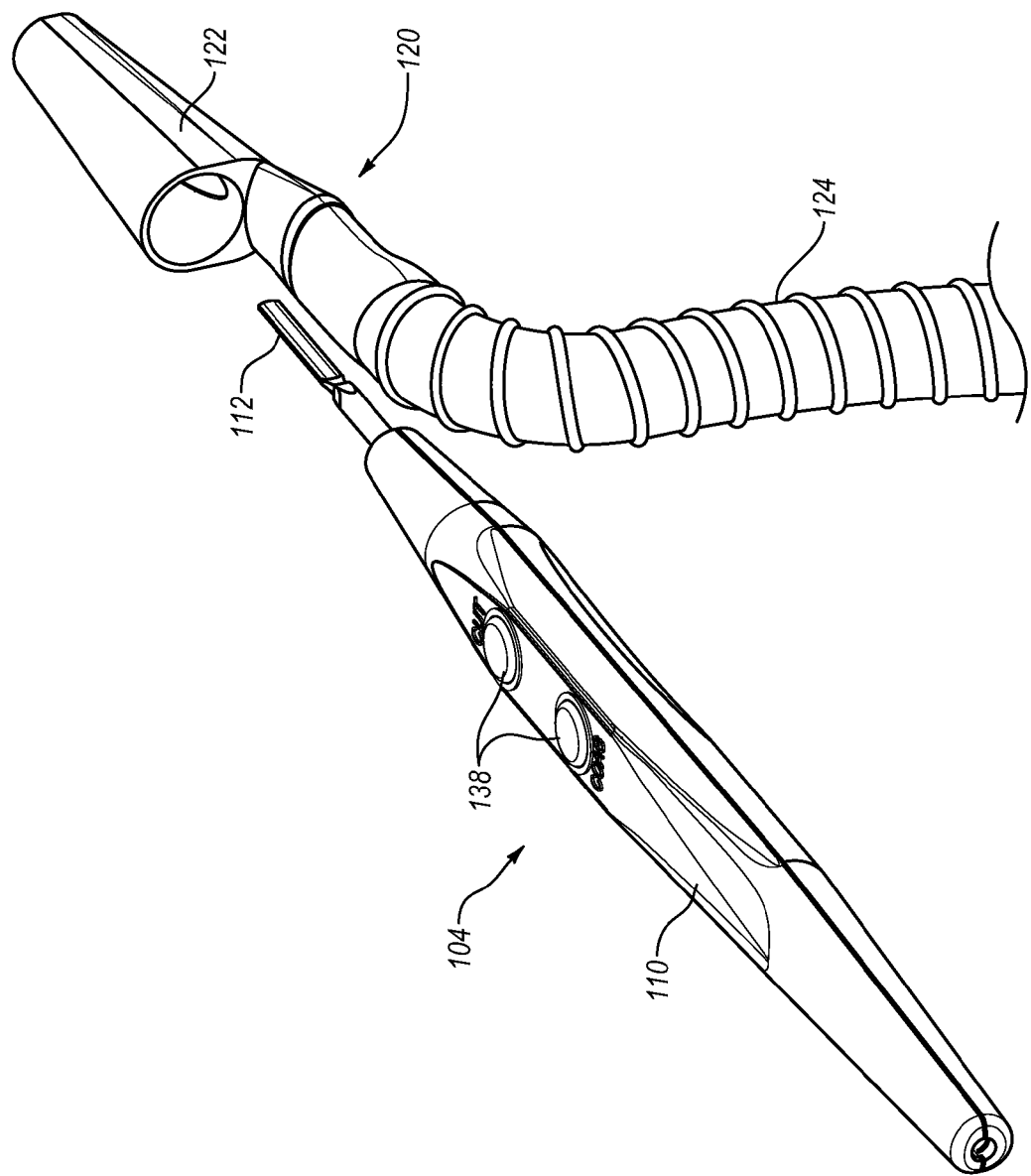
FIG. 3 illustrates an exploded view of the electrosurgical instrument and the fluid evacuation device of FIG. 1.
Figure 4:
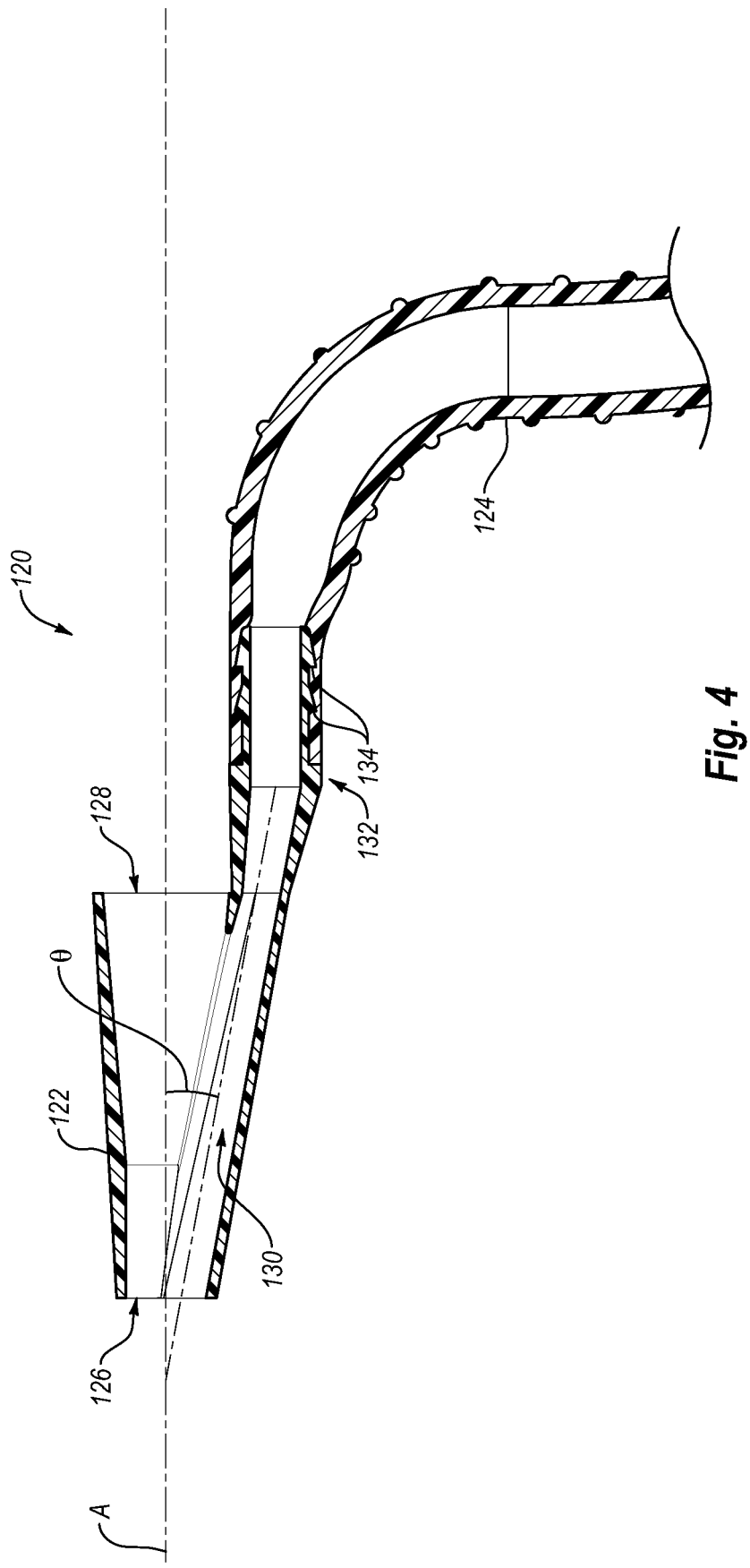
FIG. 4 is a partial cross-sectional view of the fluid evacuation device of FIG. 1.
Figure 5:
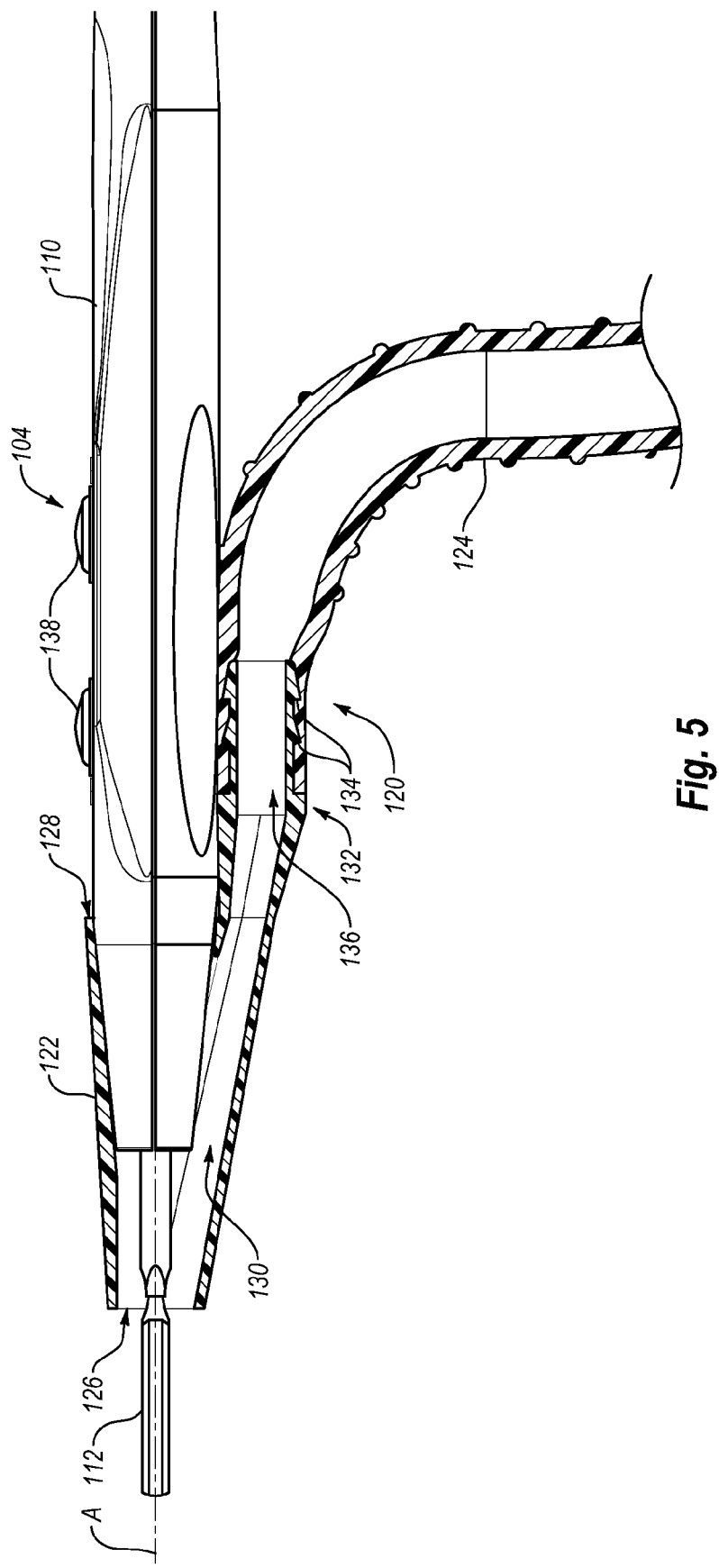
FIG. 5 is a partial cross-sectional view of the fluid evacuation device attached to the electrosurgical instrument.
Figure 6:
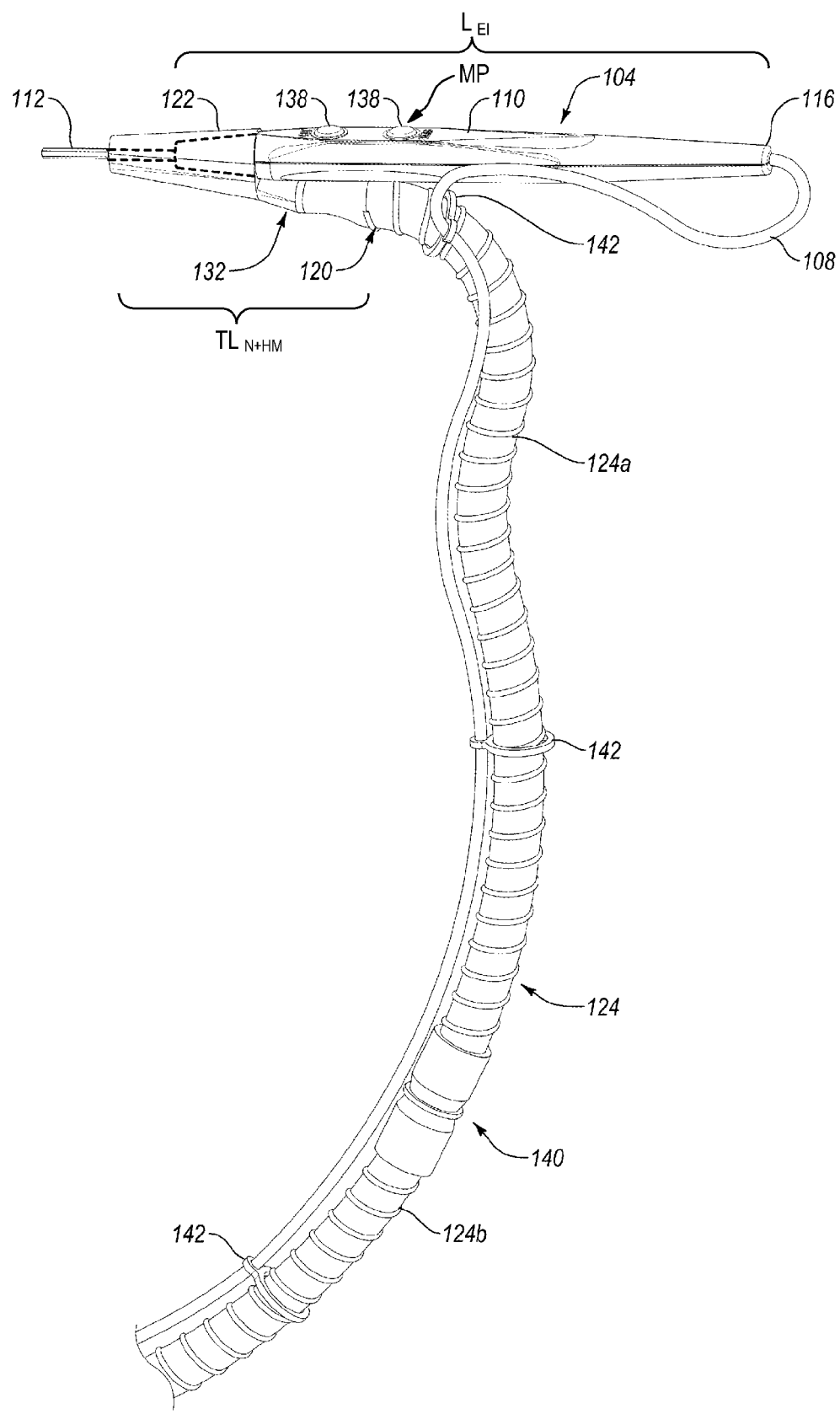
FIG. 6 is a perspective view of the electrosurgical instrument and fluid evacuation device of FIG. 1 showing a power cable of the electrosurgical instrument attached to an evacuation hose of the fluid evacuation device.
Figure 7:
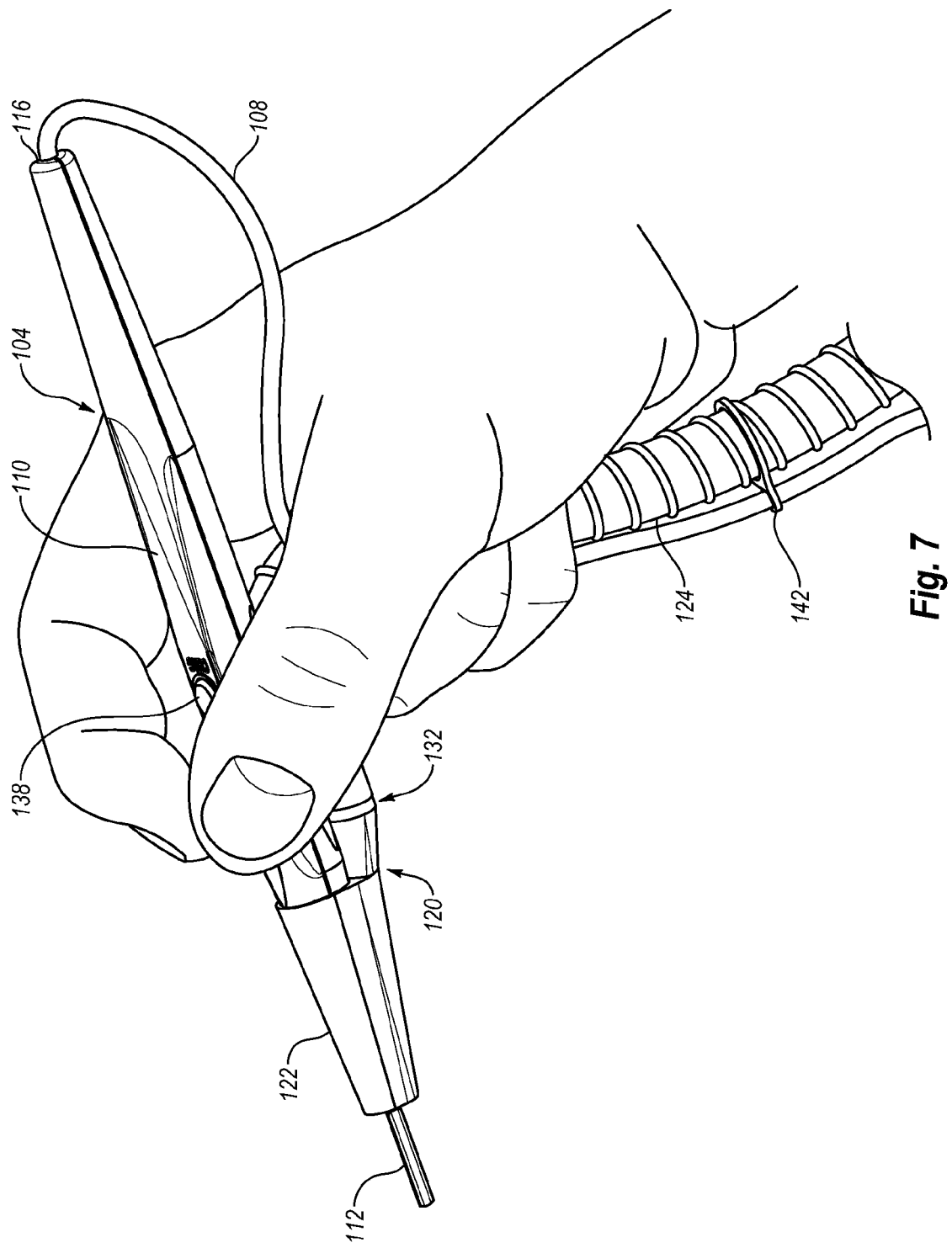
FIG. 7 illustrates an exemplary manner of holding the electrosurgical instrument and fluid evacuation device of FIG. 1.
Figure 8:
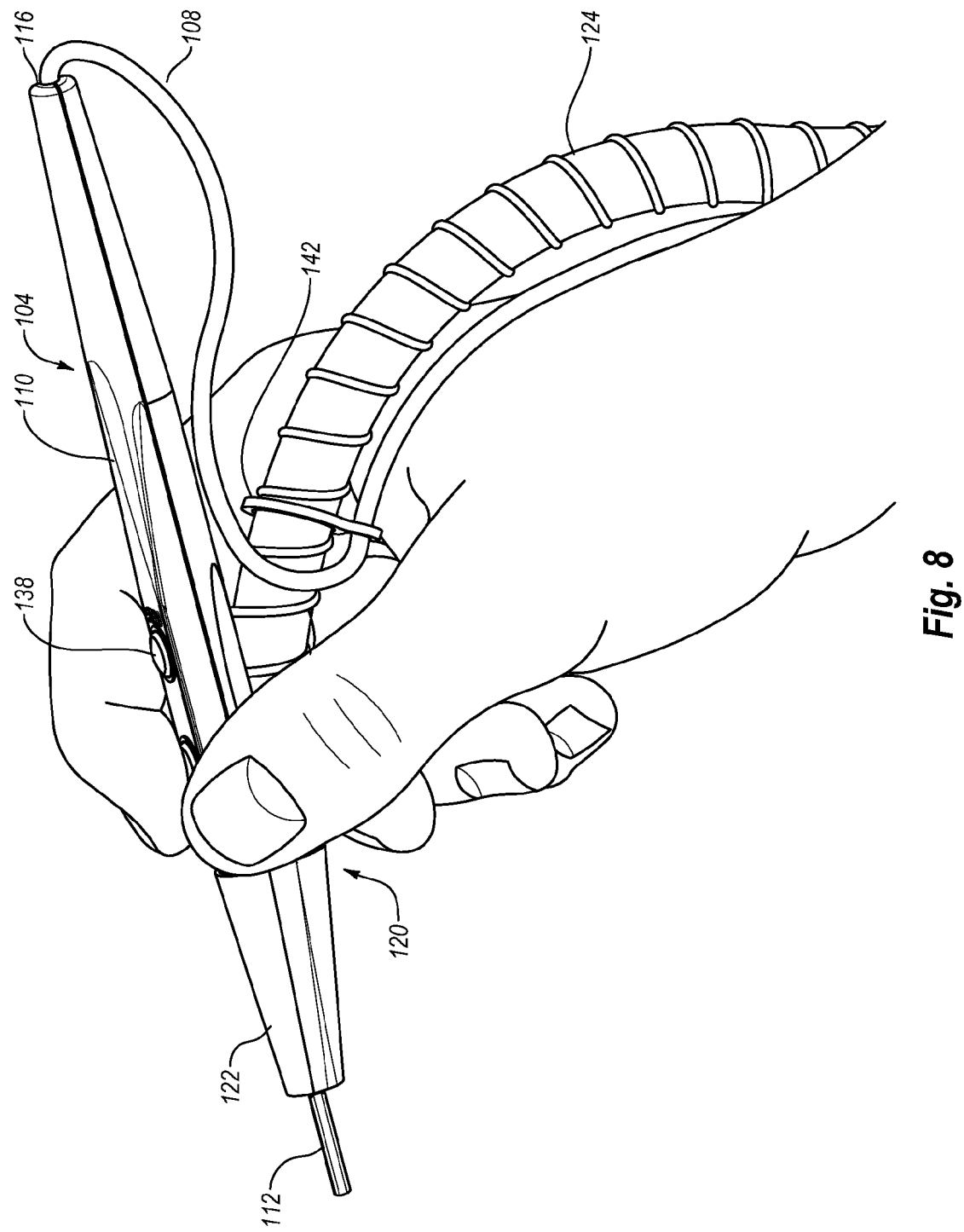
FIG. 8 illustrates another exemplary manner of holding the electrosurgical instrument and fluid evacuation device of FIG. 1.

Attention is now directed back to FIG. 1 as well as to FIGS. 3-8. FIG. 3 illustrates an exploded view of fluid evacuation device 120 removed from electrosurgical instrument 104. FIG. 4 illustrates a cross-sectional view of fluid evacuation device 120. FIG. 5 illustrates a cross-sectional view of fluid evacuation device 120 mounted on electrosurgical instrument 104. FIG. 6 illustrates electrosurgical instrument 104 with fluid evacuation device 120 mounted thereon and clips securing cable 108 and evacuation hose 124 together. FIGS. 7 and 8 illustrate exemplary manners of holding electrosurgical instrument 104 and fluid evacuation device 120.

As can be seen in the Figures, nozzle 122 includes an opening 126 in the distal end thereof. Opening 126 is sized to allow electrode tip 112 to extend therethrough. Additionally, opening 126 is sized to allow fluid to flow through opening 126 into nozzle 122 and around electrode tip 112.

Nozzle 122 also includes a receptacle 128 that opens towards the proximal end of nozzle 122. Receptacle 128 is configured to receive and selectively retain therein at least a portion of the distal end or nose 118 of hand piece 110. Receptacle 128 may be shaped or otherwise formed to generally conform to nose 118 of hand piece 110, thereby creating a friction fit when hand piece 110 is inserted into nozzle 122. Additionally or alternatively, receptacle 128 may include other features that facilitate a secure connection between nozzle 122 and hand piece 110. For instance, an interior surface of receptacle 128 may include a deformable material (e.g., foam, rubber) that conforms to the shape of hand piece 110 to assist with retaining hand piece 110 therein as well as providing an effective seal between the two. In other embodiments, receptacle 128 may include one or more clamps, clips, protrusions, or other features that selectively or permanently secure nozzle 122 onto distal end 118 of hand piece 110. Furthermore, nozzle 122 may be selectively or permanently connectable to hand piece 110.

As best seen in FIGS. 4 and 5, receptacle 128 and opening 126 are in fluid communication with one another and share a common axis A. As a result, when electrosurgical instrument 104 is inserted into receptacle 128, electrode tip 112 passes through nozzle 122 and out of opening 126, as shown in FIG. 5. When nozzle 122 is mounted on electrosurgical instrument 104 in this manner, axis A of nozzle 122 is generally collinear with a longitudinal axis of electrosurgical instrument 104.

Receptacle 128 is configured to limit how far electrosurgical instrument 104 may be inserted into nozzle 122. As illustrated in FIGS. 4 and 5, receptacle 128 has a generally conical or tapered shape to limit the insertion depth of electrosurgical instrument 104. More specifically, receptacle 128 narrows closer to the distal end of nozzle 122. That is, receptacle 128 is wider near the proximal end of nozzle 122 than near the distal end of nozzle 122. As a result, when electrosurgical instrument 104 is being inserted into nozzle 122, hand piece 110 will eventually engage the interior of receptacle 128 such that hand piece 110 cannot be inserted any further into nozzle 122.

In addition to opening 126 and receptacle 128, nozzle 122 also includes a flow region 130. Flow region 130 is in fluid communication with opening 126 such that fluid drawn into nozzle 122 through opening 126 is able to pass through flow region 130. In the illustrated embodiment, flow region 130 forms an angle $\Theta$ with axis A of receptacle 128.

The sizes of various portions of nozzle 122 can vary from one embodiment to another, depending on various factors, including the electrosurgical instrument it is used with, the length of the electrode tip, and the like. In the illustrated embodiment, for instance, nozzle 122 has a length (between the proximal and distal ends thereof) of about 1.5 inches. In other embodiments, however, nozzle 122 may have a length of between about 0.5 inches and about 6 inches. Similarly, while opening 126 is illustrated with a diameter of about 0.3 inches, opening 126 may have a diameter of between about 0.2 inches and about 0.75 inches. Likewise, while receptacle 128 is illustrated with a proximal opening having a diameter of about 0.5 inches, the proximal opening to receptacle 128 may range from about 0.25 inches to about 1 inch.

Extending proximally from nozzle 122, and particularly from the proximal end of flow region 130, is a hose mount 132 to which an end of evacuation hose 124 is connected. Hose mount 132 may be integrally formed with nozzle 122, or nozzle 122 and hose mount 132 may be formed separately and secured together thereafter. In the illustrated embodiment, hose mount 132 includes ridges 134 formed on an outer surface thereof. An end of evacuation hose 124 is positioned around hose mount 132 and ridges 134 assist in retaining the end of evacuation hose 124 on hose mount 132. In addition or as an alternative to ridges 134, evacuation hose 124 may also be secured to hose mount 130 using other fasteners, such as zip-ties, clamps, adhesives, or combinations thereof. Still further, evacuation hose 124 may also be heat shrunk onto hose mount 132.

As can be seen in FIGS. 4 and 5, hose mount 132 has a passageway 136 extending therethrough. Passageway 136 is in fluid communication with flow region 130 in nozzle 122. Fluid that is drawn into opening 126 may pass through flow region 130 and into passageway 136. Passageway 136 is also in fluid communication with a lumen in evacuation hose 124. Accordingly, fluid that is drawn into nozzle 122 may be conveyed away via evacuation hose 124.

Hose mount 132 and passageway 136 are illustrated as having oval cross-sectional shapes. By forming hose mount 132 and passageway 136 with oval cross-sectional shapes, the height of hose mount 132 may be reduced without having to reduce the flow volume that may pass through hose mount 132. It is understood, however, that hose mount 132 and/or passageway 136 may have other cross-sectional shapes, including circular cross-sectional shapes.

As noted above, receptacle 128 and flow region 130 form an angle Θ. The angled relationship therebetween results in hose mount 132 being offset from axis A. Offsetting hose mount 132 from axis A causes hose mount 132 to be positioned to a side of hand piece 110. As can be seen in FIG. 5, for instance, hose mount 132 is disposed along the underside or belly of hand piece 110.

As with nozzle 122, the sizes of hose mount 132 can vary from one embodiment to another, depending on various factors, including the electrosurgical instrument it is used with, the evacuation hose used in connection therewith, and the like. In the illustrated embodiment, hose mount 132 has a length (between the proximal and distal ends thereof) of about 1 inch. As a result, when fluid evacuation device 120 is mounted on electrosurgical instrument 104, hose mount 132 extends proximally along hand piece 110 to the region of hand piece generally below the user inputs 138 on electrosurgical instrument 104. In FIG. 5, for instance, hose mount 132 extends along hand piece 110 to the area below a distal user input 138. Thus, in some example embodiments, such as that shown in FIG. 6, nozzle 122 and hose mount 132 are disposed entirely distal of the midway point MP of electrosurgical instrument 104. As illustrated in FIG. 6, the midway point MP is near user inputs 138. In some embodiments, nozzle 122 and hose mount 132 can have a total length $TL_{N+HM}$ that is less than about half the length $L_{EI}$ of electrosurgical instrument 104.

Although hose mount 132 is illustrated has having a length of about 1 inch, hose mount 132 may have a length of between about 0.2 inches to about 3 inches or more. Thus, in some embodiments, hose mount 132 and nozzle 122 can have a total length of between about 2 inches and about 6 inches or between about 0.7 inches and about 6 inches. Similarly, passageway 136 may have an inner diameter of between about 0.2 inches and about 3 inches. In other embodiments, hose mount 132 may be effectively incorporated into nozzle 122, rather than extending proximally therefrom. For instance, flow region 130 may have a receptacle that is configured to receive and retain an end of evacuation hose 124 therein.

As can be seen in the Figures, evacuation hose 124 may be relatively flexible. As a result, evacuation hose 124 may extend away from electrosurgical instrument 104 at various angles and from various positions (referred to herein after as "extension locations") along the length of electrosurgical instrument 104.

As best seen in FIG. 6, evacuation hose 124 may include two or more sections that are connected together in a manner that allows for relative movement between adjacent sections. For instance, evacuation hose 124 may include a first section 124a and a second section 124b that are connected together via a swivel 140. Swivel 140 may include a first half and a second half that are able to rotate relative to one another. First section 124a may be connected to the first half of swivel 140 and second section 124b may be connected to the second half of swivel 140. The ability of the first and second halves of swivel 140 to rotate relative to one another enables first and second sections 124a, 124b of evacuation hose 124 to also rotate relative to one another. As a result, nozzle 122, hand piece 110, and first section 124a are able to move and rotate relative to second section 124b with less longitudinal rotational torque.

At least a portion of evacuation hose 124 may be corrugated, convoluted, fluted, or have detents disposed on the outer surface thereof. In other embodiments, evacuation hose 124 may not be corrugated, convoluted, fluted, or include detents thereon. Rather, evacuation hose 124 may have a smooth outer surface.

FIG. 6-8 illustrate cable 108 secured to evacuation hose 124 via clips 142. In the illustrated embodiment, each of clips 142 includes a ring disposed around evacuation hose 124 to secure clips 142 to evacuation hose 124. The rings of clips 142 may extend entirely around evacuation hose 124, or the rings may extend only partially around evacuation hose 124 so that evacuation hose 124 may be selectively removed from the rings through an opening. In addition, each of clips 142 also includes a hook in which cable 108 may be secured. Cable 108 may be selectively connected to clips 142 or permanently connected thereto.

In the illustrated embodiment, clips 142 are disposed on evacuation hose 124 at various locations. In some embodiments, clips 142 may be fixedly disposed at the various locations along the length of evacuation hose 124. In other embodiments, clips 142 may be movably disposed on evacuation hose 124 such that a user can adjust the position of one or more of clips 142 along the length of evacuation hose 124. Furthermore, although the present embodiment is illustrated with three clips 142, it is understood that other embodiments may include one or more clips 142.

It is also understood that cable 108 and evacuation hose 124 may be connected together with mechanisms other than clips 142. Merely by way of example, cable 108 and evacuation hose 124 may be secured together with zip ties, cords, a hook and loop fastener, such as VELCRO, cohesive or self-adhesive tape, such as COBAN, and the like. Thus, cable 108 and evacuation hose 124 can be secured together with any suitable fastener, whether the fastener provides a selective or permanent connection between cable 108 and evacuation hose 124.

Securing cable 108 and evacuation hose 124 together can provide various benefits. For instance, when connected together as shown, cable 108 and evacuation hose 124 extend away from hand piece 110 together. As a result, cable 108 and evacuation hose 124 are less likely to become tangled with one another, a user, or other equipment.

Securing cable 108 and evacuation hose 124 together as shown can also dramatically reduce the resistance typically created by cable 108. As can be seen in FIGS. 6-8, cable 108 extends out of proximal end 116 of hand piece 110. Rather than hanging down from proximal end 116 (as shown in FIG. 2), however, cable 108 extends distally along the length of hand piece 110 until it meets and connects to evacuation hose 124. Thus, as best seen in FIG. 6, cable 108 and evacuation hose 124 extend away from hand piece 110 at about the same location along the length of hand piece 110. In the illustrated embodiment, the extension location of cable 108 and evacuation hose 124 is at about the middle of hand piece 110.

As noted herein, a cable or hose that extends from a proximal end of a hand piece creates resistance, typically in the form of a torque, to the movement of the hand piece. Thus, when a user manipulates the hand piece, either to move the hand piece to a new location or to reorient the hand piece within the same general location, the cable or hose resists the movement or reorientation of the hand piece. Accordingly, allowing the evacuation hose 124 and/or cable 108 to extend away from hand piece 110 at a more distally located position reduces the amount of resistance typically created by the cable or hose.

In addition to reducing the overall resistance typically created by a cable or hose, having cable 108 and/or evacuation hose 124 extend away from hand piece 110 closer to the distal end of hand piece 110 also reduces the change is resistance experienced when moving or reorienting hand piece 110. As a hand piece is moved or reoriented, the resistance created by a cable or hose changes. While the change in resistance may be due at least in part to the direction of movement or reorientation and/or the speed of the movement, the change in resistance is primarily due to the location along the length of the hand piece where the cable and/or hose extend away from the hand piece. As discussed herein, the increased distance between the location where the cable and/or hose extend away from the hand piece and the pivot point of the hand piece creates a larger torque. As a result, when the extension location of the cable or hose is at or near the proximal end of the hand piece, the change in resistance during movement or reorientation of the hand piece is greater than the change in resistance created when the extension location is closer to the distal end of the hand piece.

With reference to FIG. 2, for instance, when cable 108 extends out of proximal end 116 of hand piece 110, cable 108 creates resistance to the movement of hand piece 110. Additionally, as hand piece 110 is moved or reoriented, the resistance created by cable 108 changes. When cable 108 extends away from hand piece 110 from a location closer to the distal end 118 of hand piece 110, as shown in FIGS. 6-8, the resistance created by cable 108 is reduced. Additionally, the change in resistance created by cable 108 when hand piece 110 is moved or reoriented is also reduced when the extension location of cable 108 is disposed toward distal end 118 of hand piece 110. When cable 108 extends away from hand piece 110 closer to distal end 118 of hand piece 110, the resistance and change in resistance created by cable 108 falls dramatically. In such arrangements, the resistance and change in resistance may drop to near zero or at least negligible levels.

The following tables demonstrate that the amount of torque resulting from a distally located extension location is significantly lower than when the extension location is disposed at or near the proximal end of a hand piece. The torque resulting from the cables and/or hoses connected to numerous hand pieces were measured. Specifically, the torques associated with twelve different devices were measured at various heights and at various orientations. Devices 1-4 were standard electrosurgical instruments that include power cables extending from the proximal ends of the hand pieces. Device 5 consisted of Device 1 (a standard electrosurgical instrument) retrofitted with a smoke evacuation device. The smoke evacuation device used in connection with Device 5 included a nozzle that connected to the nose of the electrosurgical instrument and an evacuation hose that extended away from the electrosurgical instrument at the proximal end of the instrument. Devices 6-11 were electrosurgical instruments that include both power cables and smoke evacuation hoses extending from the proximal ends of the hand pieces. The torque associated with electrosurgical instrument 104 and fluid evacuation device 120 was also measured with cable 108 and evacuation hose 124 extending from hand piece 110 about 0.6 inches behind (i.e., in the proximal direction) the proximal-most user input button 138, similar to the configuration shown in FIG. 6.

Table 1 includes the torques associated with the twelve devices when the hand pieces were in a level orientation (i.e., the proximal and distal ends of the hand pieces were at substantially the same height). In contrast, Table 2 includes the torques associated with the twelve devices when the hand pieces were held at a 45° angle with the distal end of the hand piece being disposed lower than the proximal end. In addition to measuring the torques when the devices were at different orientations, the torques were also measured when the hand pieces were held at different heights (i.e., 2.5 ft, 3 ft, 3.5 ft, and 4 ft).

Tables 1 and 2 also include other basic information regarding each of the evaluated devices. This information includes the lengths of the hand pieces, the masses of the hand piece and associated cables/hoses, and the distances between the pivot points of the hand pieces and the ends of the hand pieces. To provide consistency throughout the samples, the pivot point for each hand piece was determined to be at the user input button positioned closest to the proximal end of the hand piece.

TABLE 1

| | Height above floor | | | | Center of | Center of Proximal Input | | Mass of hand |
|---|---|---|---|---|---|---|---|---|
| | 2.5 ft | 3.0 ft | 3.5 ft | 4.0 ft | Proximal Input Button to Tip (in.) | Button to exit location (in.) | Total (in.) | piece, cord, & tubing (g) |
| | Torque (oz. in.) | | | | | | | |
| Device 1 | 1.25 | 1.5 | 1.75 | 2 | 3.82 | 3.82 | 7.64 | 73.24 |
| Device 2 | 2 | 2.5 | 3 | 3.5 | 3.85 | 3.8 | 7.65 | 104.19 |
| Device 3 | 0.65 | 0.9 | 1.2 | 1.5 | 4.1 | 3.82 | 7.92 | 62.69 |
| Device 4 | 0.65 | 0.8 | 1 | 1.25 | 4.2 | 3.3 | 7.50 | 66.3 |
| Device 5 | 6 | 7.5 | 8 | 9 | 3.82 | 5.24 | 9.06 | 156.22 |
| Electrosurgical Instrument 104 w/Fluid Evac Device 120 (cable and evac hose extending near input button) | 0 | 0 | 0 | 0 | 3.82 | 0.6 | 4.42 | 154.91 |
| Device 6 | 4.5 | 5.5 | 6.5 | 7 | 4.2 | 4 | 8.20 | 216.27 |
| Device 7 | 1.75 | 3 | 4.5 | 7.5 | 3.97 | 3.96 | 7.93 | 268.73 |
| Device 8 | 4.5 | 5.5 | 6.5 | 7.5 | 3.33 | 3.5 | 6.83 | 180.87 |

TABLE 1-continued

|  | Height above floor | | | | Center of Proximal Input Button to Tip (in.) | Center of Proximal Input Button to exit location (in.) | Total (in.) | Mass of hand piece, cord, & tubing (g) |
| --- | --- | --- | --- | --- | --- | --- | --- | --- |
|  | 2.5 ft | 3.0 ft | 3.5 ft | 4.0 ft |  |  |  |  |
|  | Torque (oz. in.) | | | |  |  |  |  |
| Device 9 | 3.75 | 5.75 | 6 | 6.75 | 4.43 | 3.7 | 8.13 | 141.64 |
| Device 10 | 3.25 | 4.5 | 5.25 | 6.25 | 4.24 | 4.24 | 8.48 | 157.88 |
| Device 11 | 1.5 | 1.75 | 2 | 2.25 | 4.12 | 2.57 | 6.69 | 128.73 |

TABLE 2

|  | Height above floor | | | | Center of Proximal Input Button to Tip (in.) | Center of Proximal Input Button to exit location (in.) | Total (in.) | Mass of hand piece, cord, & tubing (g) |
| --- | --- | --- | --- | --- | --- | --- | --- | --- |
|  | 2.5 ft | 3.0 ft | 3.5 ft | 4.0 ft |  |  |  |  |
|  | Torque (oz. in.) | | | |  |  |  |  |
| Device 1 | 1.5 | 1.75 | 2 | 2.3 | 3.82 | 3.82 | 7.64 | 73.24 |
| Device 2 | 2.25 | 2.75 | 3.25 | 3.5 | 3.85 | 3.8 | 7.65 | 104.19 |
| Device 3 | 0.7 | 1.25 | 1.5 | 1.75 | 4.1 | 3.82 | 7.92 | 62.69 |
| Device 4 | 1 | 1.25 | 1.5 | 1.75 | 4.2 | 3.3 | 7.50 | 66.3 |
| Device 5 | 7 | 8 | 9.5 | 11 | 3.82 | 5.24 | 9.06 | 156.22 |
| Electrosurgical Instrument 104 w/Fluid Evac Device 120 (cable and evac hose extending near input button) | 2 | 2 | 2 | 2 | 3.82 | 0.6 | 4.42 | 154.91 |
| Device 6 | 4.5 | 5.5 | 6.5 | 7 | 4.2 | 4 | 8.20 | 216.27 |
| Device 7 | 1.75 | 3 | 4.5 | 7.5 | 3.97 | 3.96 | 7.93 | 268.73 |
| Device 8 | 4.5 | 5.5 | 6.5 | 7.5 | 3.33 | 3.5 | 6.83 | 180.87 |
| Device 9 | 3.75 | 5.75 | 6 | 6.75 | 4.43 | 3.7 | 8.13 | 141.64 |
| Device 10 | 3.25 | 4.5 | 5.25 | 6.25 | 4.24 | 4.24 | 8.48 | 157.88 |
| Device 11 | 1.5 | 1.75 | 2 | 2.25 | 4.12 | 2.57 | 6.69 | 128.73 |

As can be seen from the data in Tables 1 and 2, the power cables for the standard electrosurgical devices create torques ranging from 0.65 oz. in. to 3.5 oz. in. in the horizontal orientation and from 0.7 oz. in. to 3.5 oz. in. in the angled orientation. Similarly, the power cables and hoses for Devices 5-10 create torques ranging from 1.5 oz. in. to 11 oz. in. or more in both the horizontal and angled orientations. It is observed that the torque for each device generally increases as the height of the hand piece increases. This is understandable since the length, and thus the weight, of the suspended portion of the power cable and/or evacuation hose increases as the height of the hand piece increases.

When comparing electrosurgical instrument 104 and fluid evacuation device 120 with Device 5, which is also a standard electrosurgical instrument retrofitted with an evacuation device, it is noted that the torque from the cable and hose of Device 5 is significantly higher than the torque from cable 108 and evacuation hose 124. The difference in torque is directly related to the locations at which the cables and hoses extend away from the hand pieces. Specifically, the cable and hose of Device 5, which extended away from the proximal end of the hand piece, created torques ranging from 6 oz. in. to 11 oz. in. or more, depending on the height of the hand piece. In contrast, cable 108 and evacuation hose 124, which extended away from hand piece 110 near user inputs 138, created no torque, or negligible levels of torque, in the horizontal orientation and only 2 oz. in. of torque in the angled orientation. Thus, the distally located extension location of cable 108 and evacuation hose 124 substantially or entirely eliminates the torque typically associated with cables and hoses extending from hand pieces.

In addition to the foregoing, FIGS. 7 and 8 also illustrate exemplary manners of holding electrosurgical instrument 104 with fluid evacuation device 120 connected thereto. Specifically, FIG. 7 illustrates cable 108 and evacuation hose 124 extending away from hand piece 110 on the front side of the physician's palm so that cable 108 and evacuation hose 124 are positioned in the palm of the physician's hand. As a result, the physician may grasp cable 108 and evacuation hose 124 by wrapping some or all of his or her fingers around cable 108 and evacuation hose 124. While grasping cable 108 and evacuation hose 124, the physician may also hold hand piece 110 as shown in FIG. 7 (e.g., between the thumb and middle finger, with the index finger on top to control input devices 138).

In this arrangement, cable 108 and evacuation hose 124, but particularly evacuation hose 124, may act as a handle for electrosurgical instrument 104. Additionally, cable 108 and/or evacuation hose 124 may be formed to provide stability to electrosurgical instrument 104. For instance, evacuation hose 124 and/or cable 108 may be formed of or include tubing that is stiff enough to maintain the position or orientation of hand piece 110 when evacuation hose 124 is used as a handle. More specifically, evacuation hose 124 and/or cable 108 may be stiff enough so that evacuation hose 124 and/or cable 108 maintains hand piece 110 in its current position even when a physician lets go of hand piece 110 and is only holding evacuation hose 124 and/or cable 108. Furthermore, evacuation hose 124 and/or cable 108 may be sized to comfortably fit within a physician's hand and allow for the physician to securely hold evacuation hose 124 and/or cable 108.

To provide the above noted stability and grip functionalities, evacuation hose 124 and/or cable 124 may individually or collectively have an outer diameter of between about 0.1 inches and about 3 inches. In one example embodiment, evacuation hose 124 has an outer diameter of about 0.5 inches. Evacuation hose 124 and/or cable 108 may also have some elastic flexibility that contributes to the above-noted functionality. For instance, evacuation hose 124 may be formed to allow for evacuation hose 124 to be angled or bent without collapsing or significantly reducing the inner lumen or flow channel therein. By way of example, the material used to form the evacuation hose 124 may allow evacuation hose 124 to have a bend radius of between about 0° and about 180°. In the case of evacuation hose 124 with a bend radius of about 180°, a swivel may be connected between evacuation hose 124 and hand piece 110 to allow evacuation hose 124 to extend away from hand piece 110 as shown in the Figures. In other embodiments, all or portions of evacuation hose 124 may be segmented and joined together to provide a moving joint flexibility.

As noted, evacuation hose 124 may be formed from multiple sections. The sections of evacuation hose 124 may have diameters and/or flexibility characteristics that are difference from one another. For instance, a first section connected to the hand piece may be relatively stiff to provide the above-noted stability and grip functionalities. In contrast, a second section connected to the first section may be more flexible than the first section.

As noted herein, evacuation hose 124 and/or cable 108 may be formed by one or more cables and/or one or more hoses. Accordingly, the noted diameters and flexibilities may be a result of multiple hoses, cables, and/or combinations thereof. For instance, two or more hoses may have a combined diameter of between about 0.1 inches and about 3 inches.

Rather than holding cable 108 and/or evacuation hose 124 in his or her hand as shown in FIG. 7, a physician may select to have cable 108 and/or evacuation hose 124 lay through the crook of his or her hand, as shown in FIG. 8, so that cable 108 and/or evacuation hose 124 extends down the crook of the hand towards the wrist.

While the embodiments disclosed herein have been directed to fluid evacuation devices being used in connection with electrosurgical instruments, the present disclosure is not intended to be so limited. Rather, the present disclosure is broadly directed to fluid evacuation devices that may be used in connection with any hand-held instrument. By way of non-limiting example, the fluid evacuation devices of the present disclosure may be used with such hand-held instruments as dental instruments (e.g., drills, polishing tools, scalers, compressed air tools, suction tools, irrigation tools, carries detection tools, water flossing tool (e.g., waterpik)), soldering tools (e.g., heated tools, smoke collection tools, de-soldering tools), high speed grinding and polishing tools (e.g., Dremel tools, carving tools, manicure tools, dental lab grinders/polishers), laser treatment instruments, laser surgical instruments, light probes, suction handles (e.g., Yankauer), blasting tools (e.g., sandblast, gritblast), shockwave therapy tools, ultrasonic therapy tools, ultrasonic probe tools, ultrasonic surgical tools, adhesive application instruments, glue guns, pneumatic pipettes, welding tools, RF wrinkle therapy hand pieces, phaco hand pieces, shears, shaver, or razor hand pieces, micro drill hand pieces, vacuum hand pieces, small parts handling hand pieces, tattoo needle handles, small torch hand pieces, electrology hand pieces, low speed grinding, polishing and carving tools, permanent makeup hand pieces, electrical probe hand pieces, ferromagnetic surgical hand pieces, surgical suction instruments (e.g., liposuction cannulas), surgical suction cannulas, microdermabrasion hand pieces, fiberoptic camera handles, microcamera hand pieces, pH probe hand pieces, fiberoptic and LED light source hand pieces, hydrosurgery hand pieces, orthopedic shaver, cutter, burr hand pieces, wood burning tools, electric screwdrivers, electronic pad styluses, and the like.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A hand-held instrument and fluid evacuation device kit, the hand-held instrument and fluid evacuation device kit comprising:
 a hand-held instrument that includes a proximal end, a distal end, a power cable attached to the proximal end, and one or more user inputs;
 a fluid evacuation device that is selectively attachable to the hand-held instrument, the fluid evacuation device comprising:
  a nozzle having a proximal end and a distal end, the proximal end having a receptacle configured to receive a portion of the hand-held instrument therein, the distal end having an opening therein through which fluid may be drawn into the nozzle, the nozzle also having a flow region in fluid communication with the opening in the distal end, the flow region extending from the distal end toward the proximal end;
  a hose mount extending proximally from the proximal end of the nozzle, the hose mount having a passageway extending therethrough, the passageway being in fluid communication with the flow region in the nozzle; and
  a flexible evacuation hose connected to the hose mount such that a lumen in the evacuation hose is in fluid communication with the passageway in the hose mount; and
 one or more fasteners configured to connect together the evacuation hose and the power cable of the hand-held instrument, wherein the one or more fasteners are configured to connect together at least a portion of a length of the evacuation hose and at least a portion of a length of the power cable to form a connected length of the evacuation hose and the power cable, such that the connected length of the evacuation hose and the power cable extends away from the hand-held instrument at a location between the proximal and distal ends of the hand-held instrument.

2. The fluid evacuation device of claim 1, wherein the nozzle has a longitudinal axis extending between the proximal end and the distal end thereof.

3. The fluid evacuation device of claim 2, wherein the flow region is disposed at an angle relative to the longitudinal axis of the nozzle.

4. The fluid evacuation device of claim 2, wherein the hose mount is offset from the longitudinal axis of the nozzle.

5. The fluid evacuation device of claim 2, wherein the longitudinal axis is aligned with a longitudinal axis of the hand-held instrument when the hand-held instrument is received in the receptacle.

6. The fluid evacuation device of claim 1, wherein the hand-held instrument is selected from the group consisting of a medical instrument, a dental instrument, a soldering tool, a wood burning tool, a drill, and an adhesive applicator.

7. The fluid evacuation device of claim 1, wherein, when the fluid evacuation device is attached to the hand-held instrument, the evacuation hose extends away from the hand-held instrument between proximal and distal ends of the hand-held instrument.

8. The fluid evacuation device of claim 1, wherein the evacuation hose comprises a first section of flexible hose and a second section of flexible hose.

9. The fluid evacuation device of claim 8, wherein the evacuation hose further comprises a swivel connected between the first section and the second section to enable relative rotation between the first section and the second section.

10. The fluid evacuation device of claim 1, wherein connecting the power cable to the evacuation hose such that the connected length of the evacuation hose and the power cable extends away from the hand-held instrument at a location distal of the proximal end of the hand-held instrument substantially eliminates a torque caused by the power cable.

11. The fluid evacuation device of claim 1, wherein a total length of the nozzle and the hose mount is between about 2 inches and about 6 inches.

12. The fluid evacuation device of claim 8, wherein the second of flexible hose is more flexible than the first section of flexible hose.

13. A fluid evacuation device that is attachable to a hand-held instrument that includes a proximal end, a distal end, a power cable attached to the proximal end, and one or more user inputs, the fluid evacuation device comprising:
   a nozzle configured to be mounted on the distal end of the hand-held instrument, the nozzle comprising a receptacle for receiving the distal end of the hand-held instrument therein and a flow region extending therethrough;
   an evacuation hose connected to the nozzle, the evacuation hose having a lumen extending therethrough, the lumen being in fluid communication with the flow region in the nozzle, the evacuation hose being configured to extend away from the hand-held instrument at a location between the proximal and distal ends of the hand-held instrument; and
   one or more fasteners configured to connect together the evacuation hose and the power cable at a location between the proximal and distal ends of the hand-held instrument, such that the connected portions of the evacuation hose and the power cable extend away from the hand-held instrument at a location between the proximal and distal ends of the hand-held instrument.

14. The fluid evacuation device of claim 13, wherein the evacuation hose creates a torque of between about 0 oz. in. and about 2 oz. in. on the hand-held instrument.

15. The fluid evacuation device of claim 13, further comprising a hose mount disposed between the nozzle and the evacuation hose.

16. The fluid evacuation device of claim 13, wherein at least a portion of the evacuation hose is configured to be held as a handle in a user's hand and is stiff enough to stabilize the hand-held instrument.

17. The fluid evacuation device of claim 13, wherein the evacuation hose comprises a first section of flexible hose and a second section of flexible hose.

18. The fluid evacuation device of claim 17, further comprising a swivel connected between the first section and the second section of the evacuation hose.

19. A fluid evacuation device that is attachable to a hand-held instrument that includes a proximal end, a distal end, a midway point between the proximal and distal ends, a power cable attached to the proximal end, and one or more user inputs, the fluid evacuation device comprising:
   a nozzle configured to be mounted on the distal end of the hand-held instrument, the nozzle comprising a receptacle for receiving therein the distal end of the hand-held instrument, the nozzle having a length extending between a proximal end and a distal end thereof;
   a hose mount extending proximally from the nozzle, the hose mount having a passageway extending therethrough, the passageway being in fluid communication with the nozzle, the hose mount having a length extending between a proximal end and a distal end thereof;
   a flexible evacuation hose comprising a first section of flexible hose and a second section of flexible hose, a first end of the first section being connected to the hose mount such that a lumen in the evacuation hose is in fluid communication with the passageway in the hose mount, the evacuation hose further comprising a swivel connected between the first section and the second section to enable relative rotation between the first section and the second section; and
   one or more fasteners configured to connect together the evacuation hose and the power cable at a location between the proximal and distal ends of the hand-held instrument, such that the connected portions of the evacuation hose and the power cable extend away from the hand-held instrument at a location between the proximal and distal ends of the hand-held instrument.

20. The fluid evacuation device of claim 19, wherein the nozzle and the hose mount are disposed entirely distal of the midway point of the hand-held instrument when the fluid evacuation device is attached to the hand-held instrument.

21. The fluid evacuation device of claim 19, wherein the total length of the nozzle and the hose mount is between about 0.7 inches and about 6 inches.

* * * * *